US006344858B1

(12) United States Patent
Vuylsteke et al.

(10) Patent No.: US 6,344,858 B1
(45) Date of Patent: *Feb. 5, 2002

(54) METHOD OF EVALUATING IMAGE PROCESSING PERFORMED ON A RADIOGRAPHIC IMAGE

(75) Inventors: Pieter Paul Vuylsteke, Mortsel; Danny Jozef Janssens, Eindhout, both of (BE)

(73) Assignee: AGFA-Gevaert, Mortsel (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/883,013

(22) Filed: Jun. 26, 1997

Related U.S. Application Data

(63) Continuation of application No. 08/448,890, filed on May 24, 1995, now abandoned, which is a continuation of application No. 08/084,537, filed on Jun. 28, 1993, now abandoned.

(30) Foreign Application Priority Data

Feb. 11, 1993  (EP) .............................................. 93200378

(51) Int. Cl.[7] ................................................. G09G 5/26
(52) U.S. Cl. ....................................... 345/660; 345/670
(58) Field of Search ........................... 345/11, 127, 129, 345/131, 132, 207, 660, 667, 668, 669, 670; 348/396, 390, 568, 567; 382/131, 132, 232, 235

(56) References Cited

U.S. PATENT DOCUMENTS

| | | | | |
|---|---|---|---|---|
| 4,764,975 A | * | 8/1988 | Inoue | 345/127 |
| 4,808,987 A | * | 2/1989 | Takeda et al. | 345/127 |
| 4,955,067 A | * | 9/1990 | Shimura | 382/132 |
| 5,260,781 A | * | 11/1993 | Soloff et al. | 348/396 |
| 5,260,873 A | * | 11/1993 | Hishinuma | 345/11 |

OTHER PUBLICATIONS van Heck, A.A; "Display System for Computed Tomographic (CT) Images", SPIE Vol. 173, Application of Optical Instrumentation in Medicine VII, Mar. 1979.*

* cited by examiner

Primary Examiner—Chanh Nguyen
(74) Attorney, Agent, or Firm—Hoffman, Warnick & D'Alessandro LLC; John A. Merecki

(57) ABSTRACT

Method of evaluating image processing performed on a radiographic image.

Figure 1:
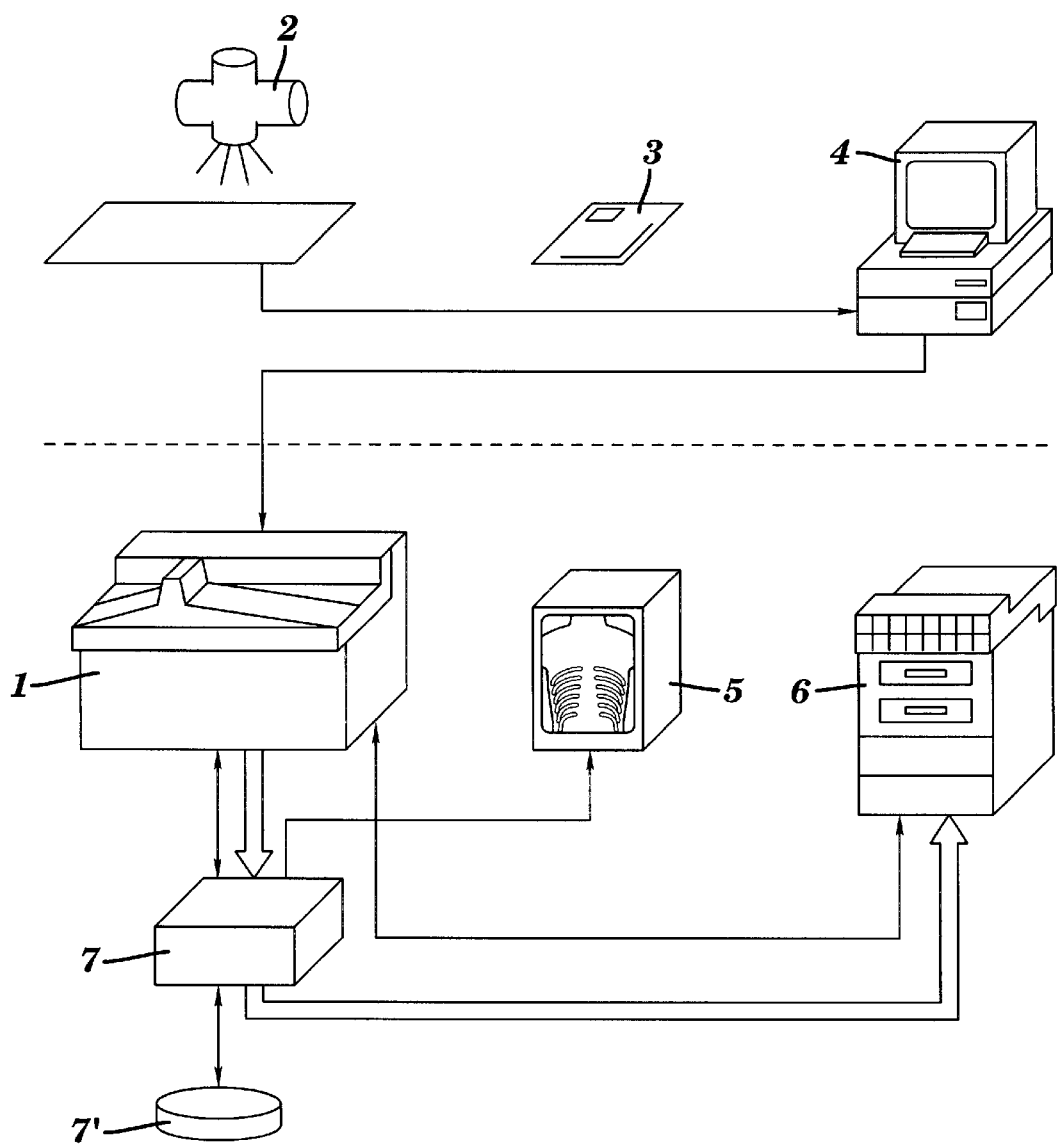

Method and apparatus for reading a radiation image stored in a photostimulable phosphor sheet or on a photographic film provided with the possibility of convenient evaluation of the performed image processing.

18 Claims, 12 Drawing Sheets

POWER FUNCTION p=0.7

METHOD OF EVALUATING IMAGE PROCESSING PERFORMED ON A RADIOGRAPHIC IMAGE

This application is a continuation of application(s) Ser. No. 08/448,890 filed on May 24, 1995, now abandoned, which is continuation of Ser. No. 08/084,537 filed on Jun. 28, 1993, now abandoned.

FIELD OF THE INVENTION

The present invention is in the field of digital radiography. The invention more specifically relates to a method and an apparatus permitting evaluation of processing performed on the digital signal representation of a radiographic image in a most convenient way.

BACKGROUND OF THE INVENTION

In the field of digital radiography a wide variety of image acquisition techniques have been developed such as computerised tomography, nuclear magnetic resonance, ultrasound, detection of a radiation image by means of a CCD sensor or a video camera etc.

In still another technique a radiation image, for example an image of x-rays transmitted by an object, is stored in a screen comprising a photostimulable phosphor such as one of the phosphors described in European patent publication 503 702 published on Sep. 16, 1992 and U.S. Ser. No. 07/842,603. The technique for reading out the stored radiation image consists of scanning the screen with stimulating radiation, such as laser light of the appropriate wavelength, detecting the light emitted upon stimulation and converting the emitted light into an electric representation for example by means of a photomultiplier.

The signal is then digitized, processed and subsequently used to control the hard copy recording in image reproducing system such as a laser recorder. For diagnostic purposes the reproduction is viewed and analysed on an lightbox.

In an alternative image acquisition system a digital representation of a radiographic image can be obtained by scanning a radiographic film carrying a radiographic image with light, detecting the image-wise modulated light (reflected or transmitted) and converting the detected light into a digital signal representation. Likewise the digital signal can be processed and can subsequently be used for controlling hard copy recording or display of the processed image.

Previous to image reproduction, the image signal can be subjected to image processing algorithms serving various kinds of purposes and involving the selection and setting of several kinds of processing parameters depending on the specific type of examination.

The different kinds of processing methods that can be applied will be described in extenso furtheron in the application. In summary these processing methods may comprise processing for the purpose of image analysis such as a method of recognising the borders of an irradiation field in case of shielded irradiation and image enhancing processing methods such as spatial frequency processing, noise reduction, gradation correction defining the relation between signal values and corresponding density values etc.

After processing the image signal is commonly sent to an output recorder for reproduction of the radiographic image on film.

The image quality or the outlook of the reproduction does not always match with the expected quality or outlook for various causes which cannot always be assessed easily due to the wide variety of actions that were performed on the image signal prior to reproduction.

When such problems occur, a common practice among radiologists using a digital radiography system of the above-named kind is to collect unsatisfactory hard-copies and to discuss anomalies with the service-technician on his inspection tour.

However, it is sometimes difficult or even impossible to recall certain processing conditions for evaluation or to reconstruct the performed signal processing.

In U.S. Pat. No. 5,004,917 a radiation image reading apparatus has been described wherein reading conditions and/or image processing conditions are established on the basis of the radiation image information which has been read from a photostimulable phosphor plate. Whether the reading and/or image processing conditions fall outside of a predetermined range or not is determined. If the reading conditions and/or the image processing conditions fall outside a predetermined range, the radiation image information and data used to establish the reading conditions and/or the image processing conditions is held in storage.

When the system suffers a fault when it is operated on trial or in actual use it is automatically put into HALT mode, then the user attempts to switch on the apparatus to recover the fault or he calls the service man. If the fault cannot be located, the service man connects a supervising unit. This unit then determines whether established read-out and/or processing parameters fall within a given range, and if negative, the supervising unit stores the reading conditions and/or processing conditions e.g. on a magnetic tape for analysis in the laboratory, so that any fault can be located and repaired.

In this system images for which the processing and/or read-out conditions fall within the predetermined range are not stored, so that in case an anomaly appears when evaluating the hard copy reproduction of such an image there is no possibility of retrieval of the image data foreseen.

SUMMARY OF THE INVENTION

It is an object of the present invention to provide a system for reading, processing and reproducing a radiation image, said system being designed so as to provide easy evaluation of the performed processing.

A further object of the invention is to provide a system of the above-named kind wherein the performed processing can be evaluated without the need of examining a hard copy of the processed image.

Further objects will become apparent from the description hereinafter.

STATEMENT OF THE INVENTION

The objects of the invention are achieved by a method of evaluating image processing performed on a digital representation of a radiation image comprising the steps of acquiring a digital representation of a radiation image, producing for said radiation image an image representation of a reduced number of pixels, storing in a storage device data identifying an image, said reduced image representation, parameters used in course of said processing and intermediate processing results.

In one embodiment a digital image representation is acquired by reading-out a radiation image that has been stored in a photostimulable phosphor screen. The read-out method comprises the steps of scanning said screen with stimulating irradiation, detecting the light emitted upon stimulation and converting the emitted light into a digital signal representation. This signal representation can then be subjected to image processing.

In an alternative embodiment of the present invention the digital signal representation is obtained by scanning a radiographic film carrying a radiation image with light, detecting image-wise modulated light and converting said detected light into a digital signal representation.

The image-wise modulation of the scanning light can be obtained through either reflection or transmission by the radiographic film. The digital signal is then processed and, in accordance with the present invention, for each read-out image an image representation of a reduced number of pixels is produced, and data identifying an image, said reduced image representation, parameters used in course of said processing and intermediate processing results are stored in a storage device for each read-out image.

Alternative systems for acquiring a digital image representation can be envisioned.

In a preferred embodiment the storage device in which the data pertaining to the radiation images are stored has a limited storage capacity and is sequentially organized so that data pertaining to N successively read-out images can be stored and that when an N+1-th image becomes available, the data pertaining to this N+1-th image are stored at the expense of the first stored image data.

The present invention provides that in case an evaluation of the processing of an image is required, the data pertaining to said image can be retrieved and transmitted to a suitable output device for evaluation. Suitable output devices are a service computer, a display monitor, a hard copy recorder etc.

The method of the present invention is advantageous for the following reasons.

It enables evaluation of the performed processing on the basis of stored digital information, there is no need for collecting hard copies of images.

In this method no preliminary selection criterion is imposed on the data that are stored. In other words, specific data are stored for every read-out image and no essential data pertaining to an image are lost or not stored (of course within the limitation as to the available storage capacity).

For every read-out picture a reduced version is stored and is kept in storage device until the full storage capacity is used. However, the storage capacity needed to perform the method of the present invention is limited since only reduced versions of the image representations are stored.

Among the data that are stored in a storage device are identification data.

In one embodiment of the present invention wherein acquisition of a digital image representation is performed by reading-out a photostimulable phosphor screen, said screen is conveyed in a cassette provided with an electrically erasable programmable read only memory.

In an identification station the patient's identification data as well as an identifier referring to a preset of processing parameters are written into the EEPROM.

Then, after exposure to x-rays the cassette is put into a read-out apparatus where the screen is taken out of the cassette and scanned with stimulating radiation. Radiation emitted upon stimulation is then directed towards a photo-multiplier or the like for conversion of the radiation into an electric signal representation.

Also in the read-out apparatus the data stored in the EEPROM on the cassette are read out. In the processing unit of the read-out device the parameters corresponding with said identifier are retrieved from a parameter table. The indentification data and the processing parameters or at least part thereof are stored for each read-out image in a storage device.

Among the data that are stored for each image are besides the identification data and the processing parameters also intermediate processing results such as the histogram of the original image, the histogram of the image after processing, a noise characterising parameter, etc.

An enumeration of the alternative processing parameters and intermediate processing results that can be stored for each read-out image are given hereinbelow with reference to the drawings.

The following is one example of a set of parameters and intermediate processing results that can be stored.

When processing a digital image signal, first a diagnostically relevant signal range can be determined by evaluation of the histogram of the image as disclosed in our co-pending European application number 91203212.5 filed Dec. 9, 1991 and U.S. Ser. No. 07/978,786.

Then, a gradation mapping function for converting signal values into density values is determined as described in our co-pending European application number 91203209.1 filed Dec. 12, 1991 and U.S. Ser. No. 07/978,091.

This method comprises the steps of
getting a canonical description of the mapping function (from the processing parameters),
getting the minimum and maximum density values (from the processing parameters),
determining maximum and minimum signal values (according to the method disclosed in the above patent application these values are deduced from two intermediary values $S_0$ and $S_1$ by proper relative alignment of the effective mapping range (i.e. the range within which mapping is defined by the above-mentioned canonical description and outside of which signal values are mapped onto said minimum and maximum density) to the relevant signal range $[S_0, S_1]$.
determining the actual mapping function.

Finally signal-to-density mapping is applied to the image.

Parameters to be determined here are minimum and maximum density value, the parameters defining the canonical form, the percentage indicating the above relative position etc. Intermediate processing results are for example the image histogram used to define the diagnostically relevant signal range, and the minimum and maximum signal values.

Since the parameters are specific for each application and can be adapted relative to the taste of a radiologist, it might happen that the result in the hard copy does not match with the radiologist's expectations.

Since the above parameters and intermediate processing results and a reduced image representation are in accordance with the present invention stored in the storage device, it is possible to retrieve them for evaluation and/or re-processing.

According to the method of the present invention, for each image a reduced version is produced being a signal representation of a smaller number of pixels than the originally acquired (e.g. read-out from stimulable phosphor screen) number of pixels.

The reduced image representation can be obtained by subsampling the image representation corresponding with the maximum of the acquired (e.g. read-out) pixels.

An alternative and preferred way of obtaining a reduced image version is deduced from an image processing method described in our copending European application number 91202079.9 filed on Aug. 14, 1991 and U.S. Ser. No. 07/924,905.

According to the processing method described in this application an image is first decomposed into a sequence of detail images at multiple resolution levels and a residual image at a resolution level lower than the minimum of said multiple resolution levels.

Next, the pixel values of said detail images are modified to yield pixel values of a set of modified detail images by applying a specific conversion function.

Next the processed image is computed by application of a reconstruction algorithm to the modified detail images and the residual image.

According to one embodiment of this method a detail image at a given resolution level is obtained by computing an approximation image, being a low-pass filtered image representation that has additionally been subsampled.

A detail image is then obtained as a pixelwise difference of the approximation image at a certain step and the approximation image at a next coarser resolution level that was also obtained as described hereinbefore, both images being brought into register by proper interpolation of the latter image.

In this preferred embodiment, the reduced image representation is then obtained as the signal representing one of the lower resolution approximation images calculated during this preferred embodiment of image enhancing processing.

This embodiment of the invention is advantageous since the additional processing time needed for calculation of the reduced version of an image representation is minimal because a reduced image version is already available in the course of the processing.

In a preferred embodiment the storage device is organized as a sequential storage device in which data pertaining to a limited number of images can be stored and in which once the storage capacity is exceeded, the data pertaining to a first stored image are lost at the benefit of data relating to a new image.

In one embodiment of the method of the present invention a kind of "freezing"-functionality may be provided, so that upon activation of said function, no data stored in the storage device can be overwritten or shifted out. This functionality is advantageous because in case very important exceptional data are read and stored, these data cannot be lost during read-out of further photostimulable phosphor screens.

A such-like functionality can be implemented in different ways, for example it is possible to prevent further filling of the sequentially organized storage device once the freeze function has been activated, so that from that moment on no image data are shifted out of the memory queue.

However, in this implementation it is not possible to add then any further new data to the same queue.

If further storage is required, another kind of memory organisation needs to be implemented. For example it is possible to empty a predetermined number of most recently filled memory locations upon activation of a freeze function and to continue filling the queue starting from the remainder of the stored images. Alternatives may be developed in dependence on the specific needs for certain applications.

In another embodiment a single image that is for example selected by scrolling through the queue of stored images and displaying the data pertaining to each of these images on the display of a user interface, can be "freezed" so that it will not be shifted out of the sequentially organized storage device. The storage and shift out of other images remains unaffected.

The invention further provides an apparatus for performing the method of the present invention.

The apparatus generally comprises means for acquiring a digital signal representation of a radiographic image, means for determining a set of processing parameters and means for processing said electric signal representation on the basis of said processing parameters. The apparatus may additionally comprise means for reproducing the processed image.

In accordance with the present invention the apparatus further comprises means for deducing from said signal representation a reduced version representing a reduced number of pixels, means for storing in respect of a predefined number of read-out images data identifying an image, processing parameters, intermediate processing results and a reduced version, means for identifying among the stored data the data pertaining to a specific image, means for retrieving said identified data, means for outputting the retrieved data.

In one embodiment means for acquiring a digital signal representation of a radiographic image comprises means for scanning a photostimulable phosphor screen with stimulating irradiation, means for detecting the light emitted upon stimulation and means for converting the detected light into a signal representation.

In an alterative embodiment means for acquiring a digital representation of an image comprises a light source, means for directing light emitted by said light source onto a radiographic film carrying a radiation image, means for detecting image-wise modulated light, means for converting image-wise modulated light into a digital signal representation.

As already mentioned hereinbefore, the apparatus may additionally comprise means for reproducing a processed image . By the words "reproduction of the processed image" in this context is meant hard copy recording as well as display.

Hard-copy recording can for example be performed by means of a laser printer. However, alternative printing techniques such as thermal printing (thermal sublimation, wax transfer, resistive ribbon etc.) may be envisioned.

In a preferred embodiment of the present invention the means for deducing a reduced version of the image signal comprise means for performing a pyramidal image decomposition.

Such processing means are described in great detail in our copending unpublished European patent application number 91202079.9 filed on Aug. 14, 1991 and U.S. Ser. No. 07/924,905.

In the course of the processing described in that application, low resolution approximation images are calculated for example by subjecting the read out image signal to consecutive low pass filtering as described below with reference to the drawings.

Hence inherent to this processing is the availability of images at lower resolution levels, so it is preferred to use and store one of these images instead of calculating a dedicated reduced image version because this would increase unnecessarily the computational effort.

The parameters that are determined and stored in the method of the present invention can generally be any kind of parameters that are used during image processing.

For example, it is possible to store the parameters relating to the window-level settings, to the gradation processing and to the processing of detail images described hereinbefore, to noise suppression processing parameters, to processing relating to the determination of a limited irradiation field in case use has been made of a shielding protector at the time of exposure of the patient to x-rays etc.

It is most convenient to store identification data, the processing parameters, the intermediate processing results and the reduced version of the processed image on the system disc. In this way an additional cost of providing additional storage medium has been avoided.

Examples of storage device organisation have been described hereinbefore when explaining the method steps of the present invention.

In one embodiment the means for identifying data pertaining to a stored image comprise a display unit that can for example be part of the user interface of the read-out apparatus.

Means are then provided to initiate upon activation a "scrolling" through the stored identification data and simultaneous display of said data on the display unit. Upon command by the operator the scrolling can be stopped when the identification data of an image which is to be evaluated are displayed. Then, retrieval of the remainder of the stored data can then be initiated and the retrieved data can be applied to an output device.

Such an output device can be a printer or a monitor. Alternatively an external storage device can be connected to the read-out apparatus (for example through the intermediary of a service computer). This embodiment provides that the data pertaining to an image to be evaluated can be loaded into the external storage device so that these data can for example be submitted to a laboratory for evaluation.

Means can also be provided for preventing at least one image from being shifted out of the sequentially organized storage device (freeze function).

Figure 2:
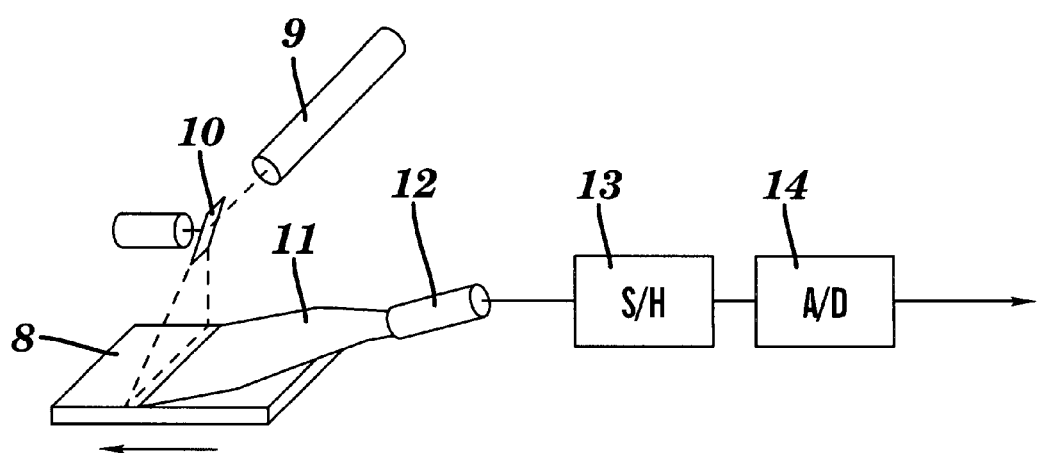
Figure 3A:
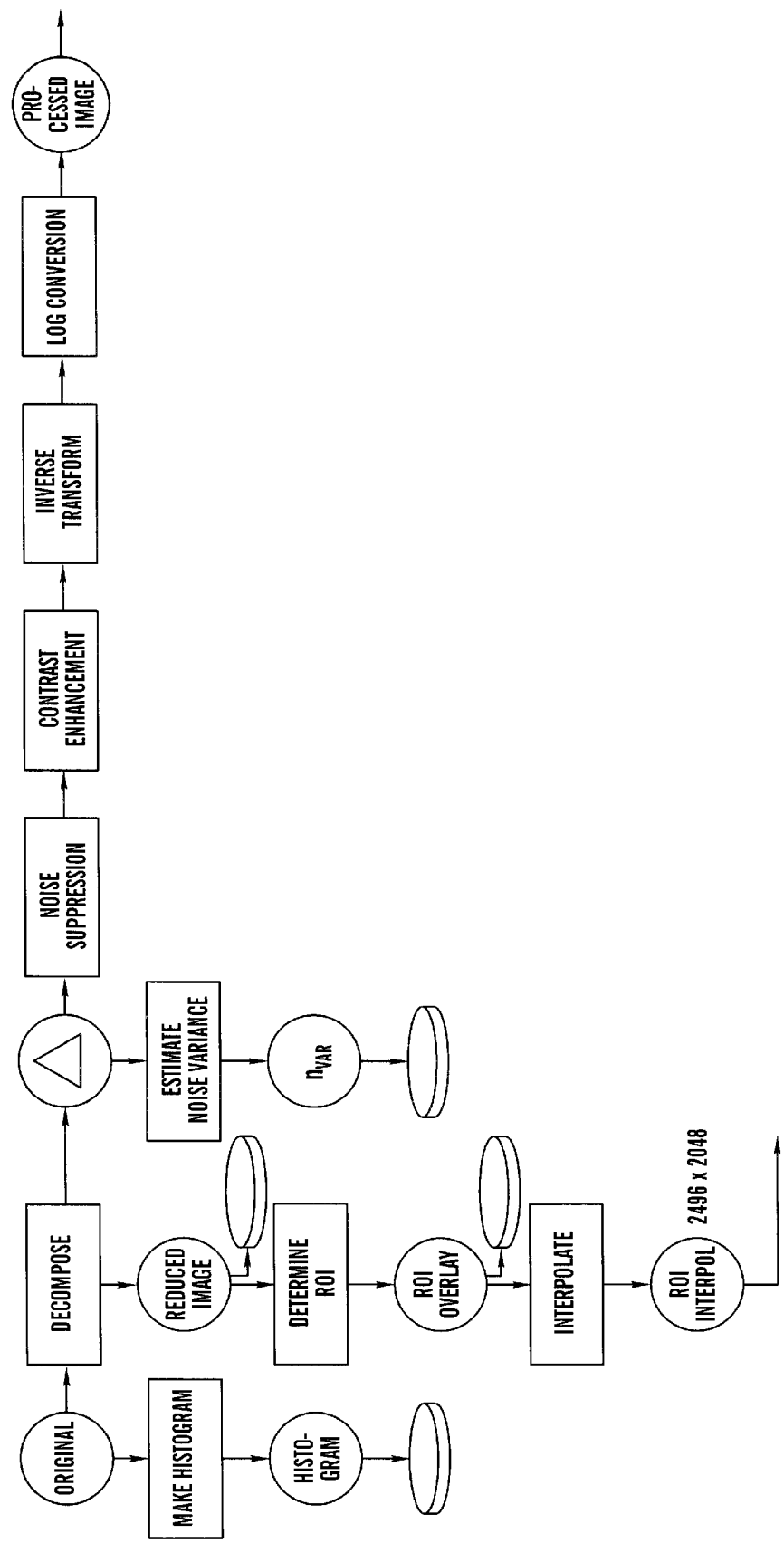
Figure 3B:
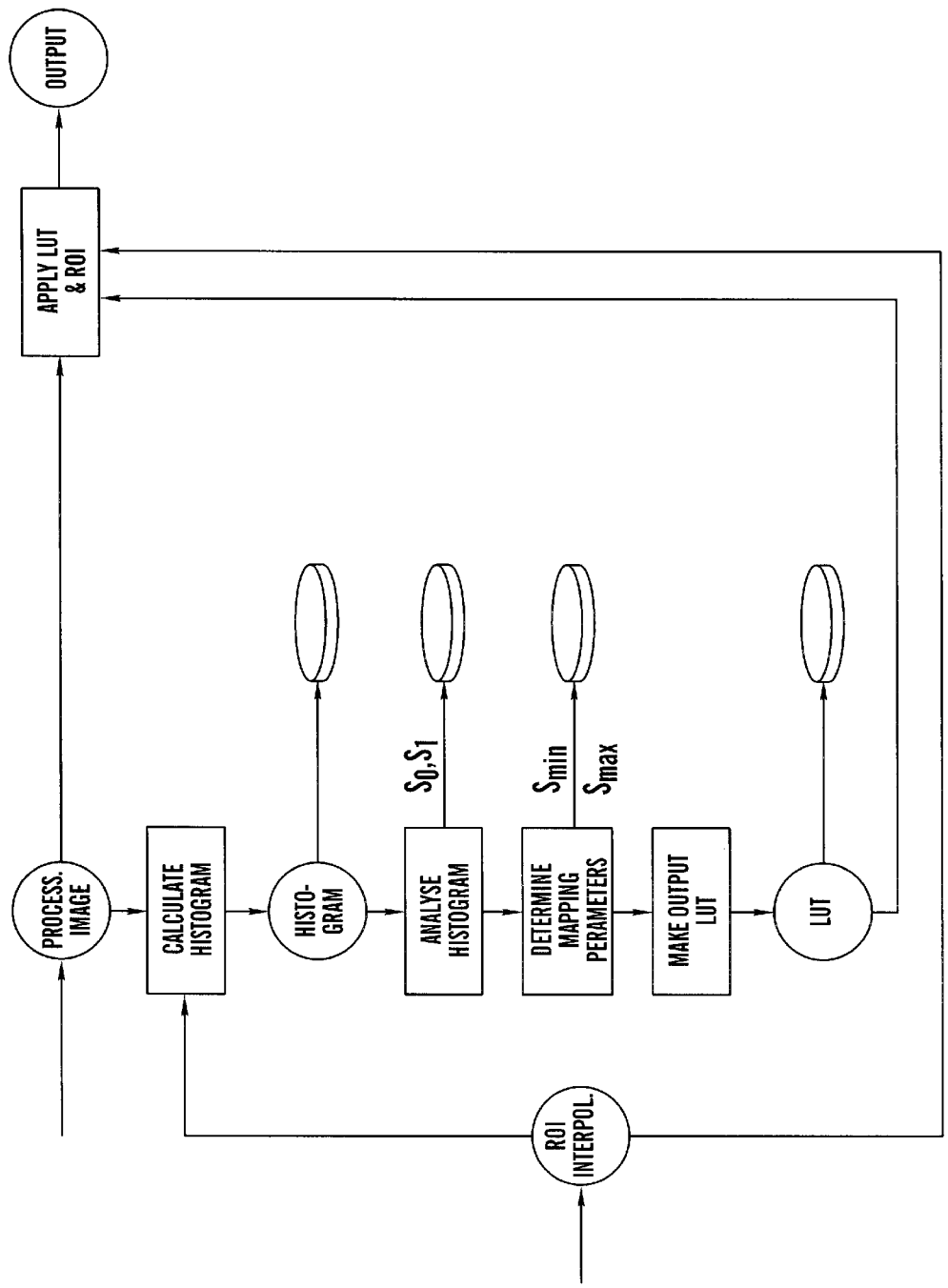
Figure 4:
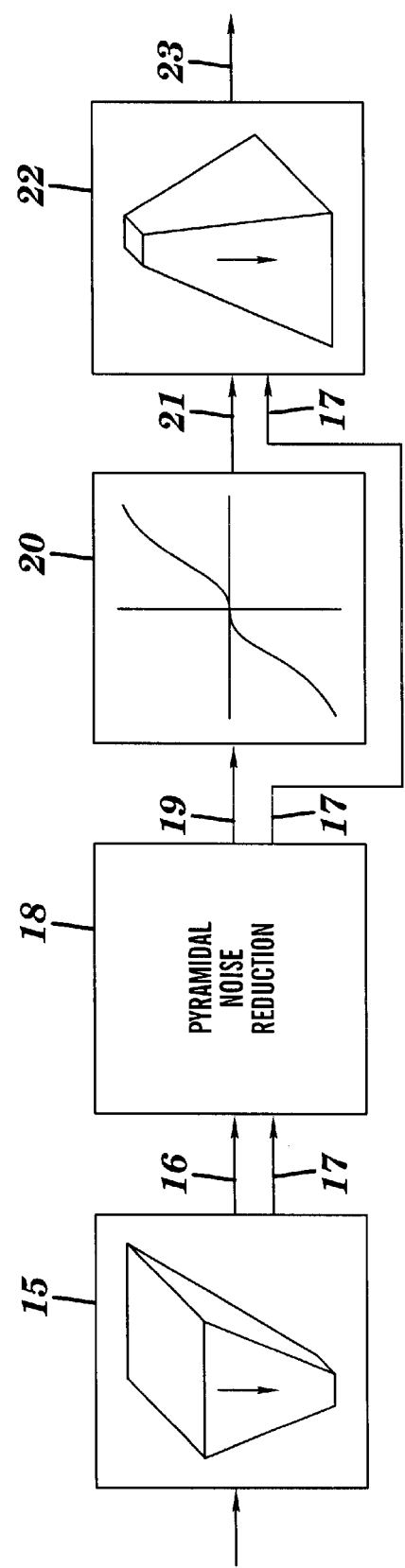
Figure 5:
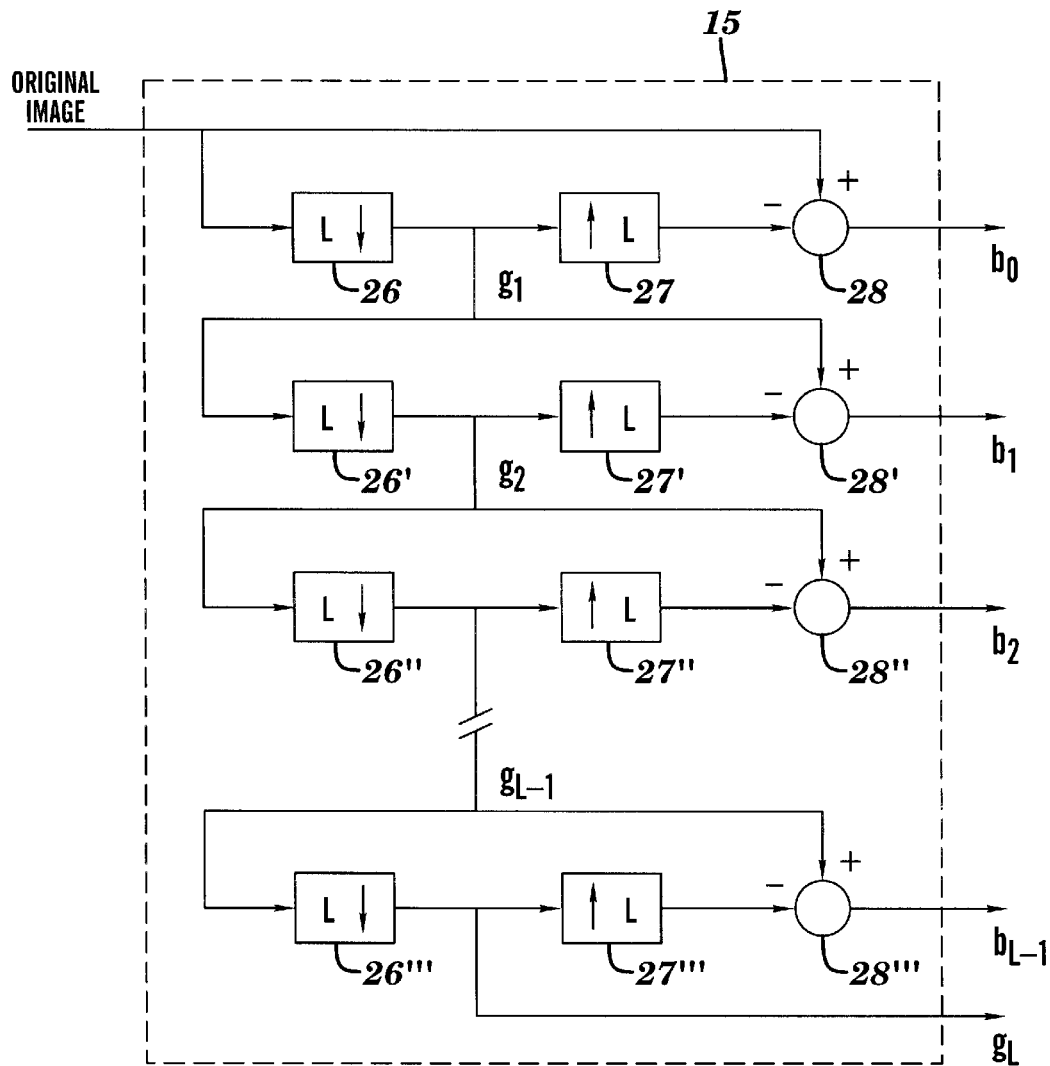
Figure 6:
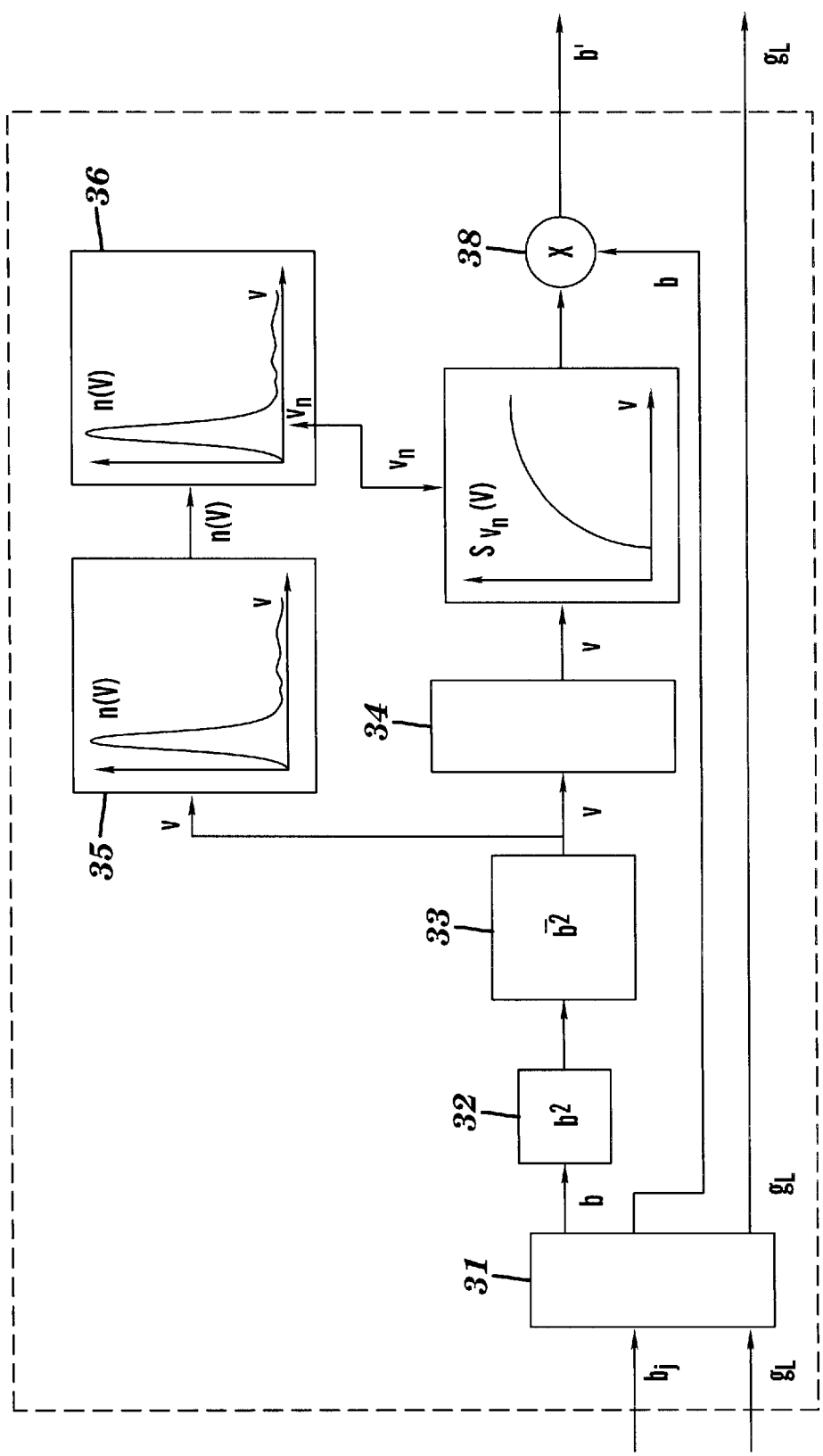
Figure 7:
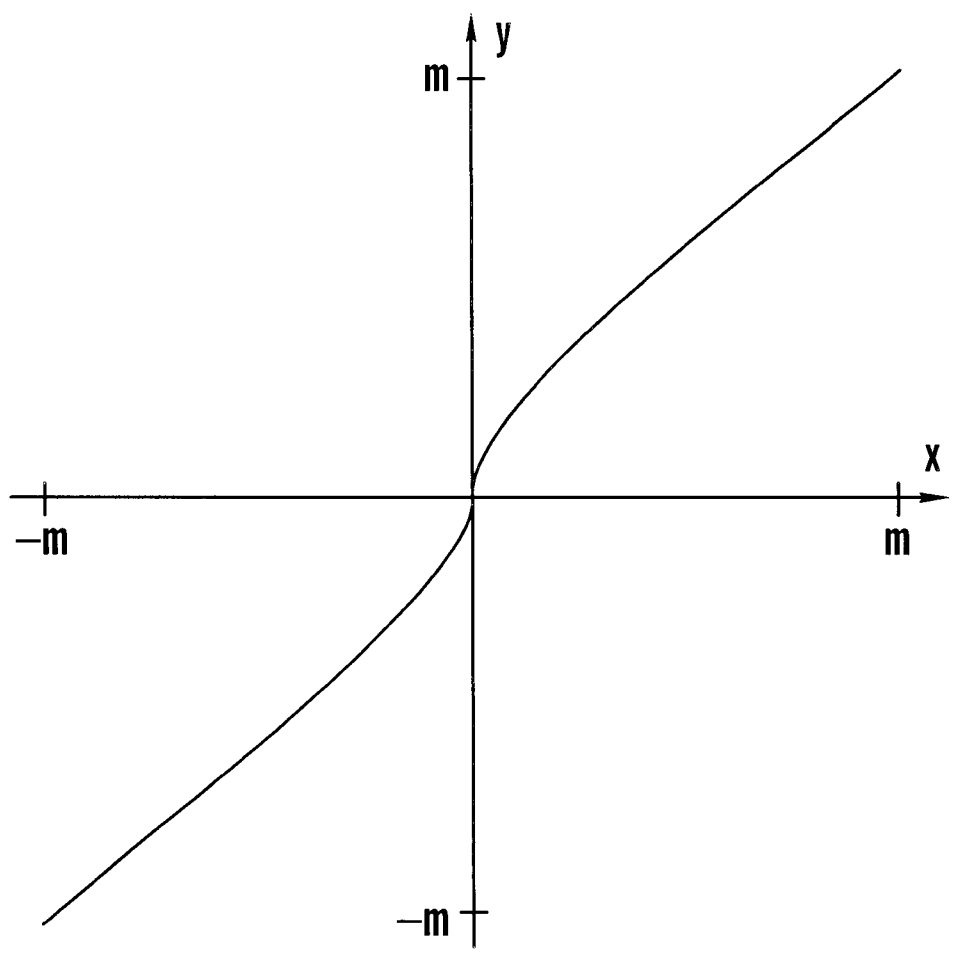
Figure 8:
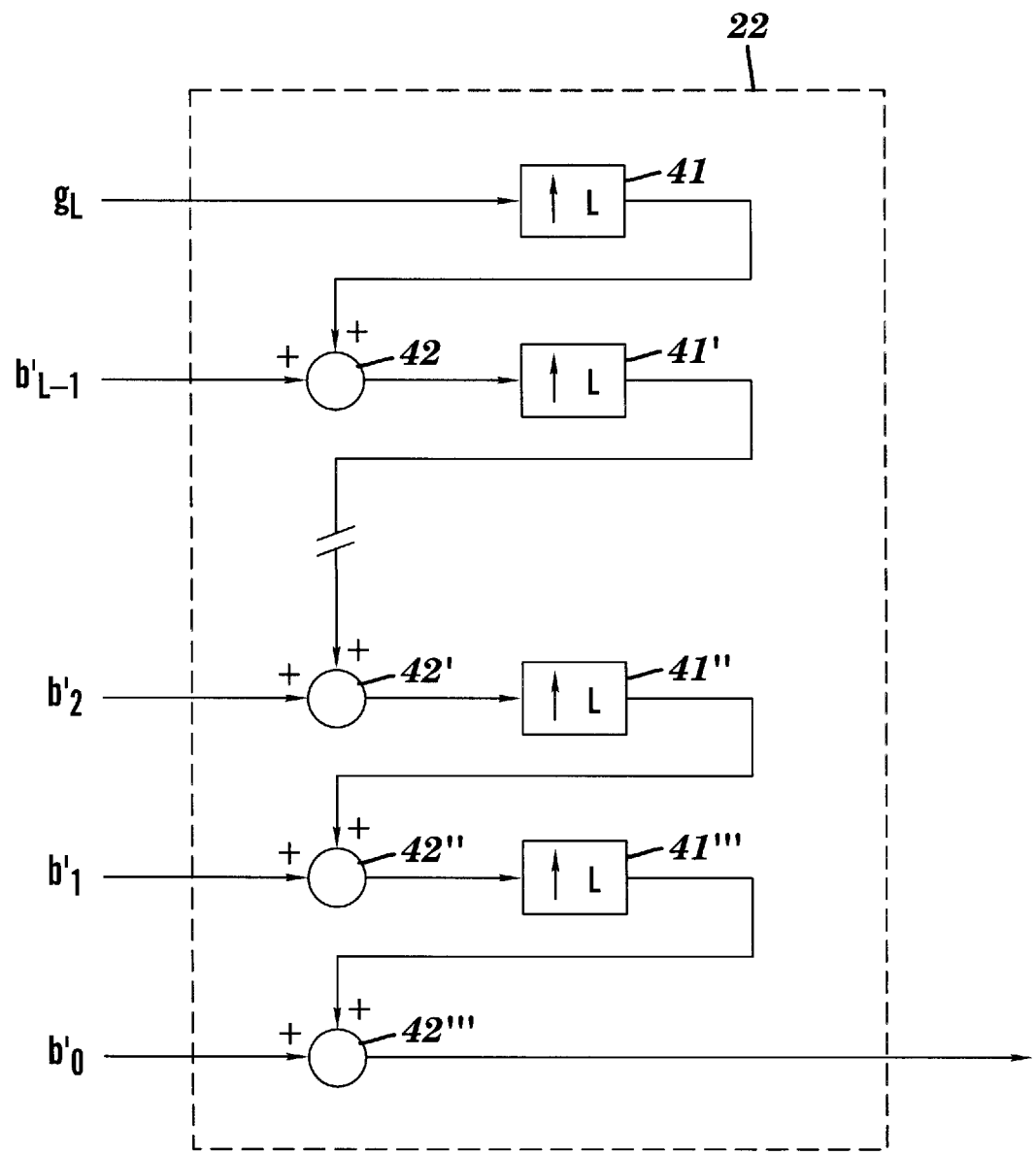
Figure 9:
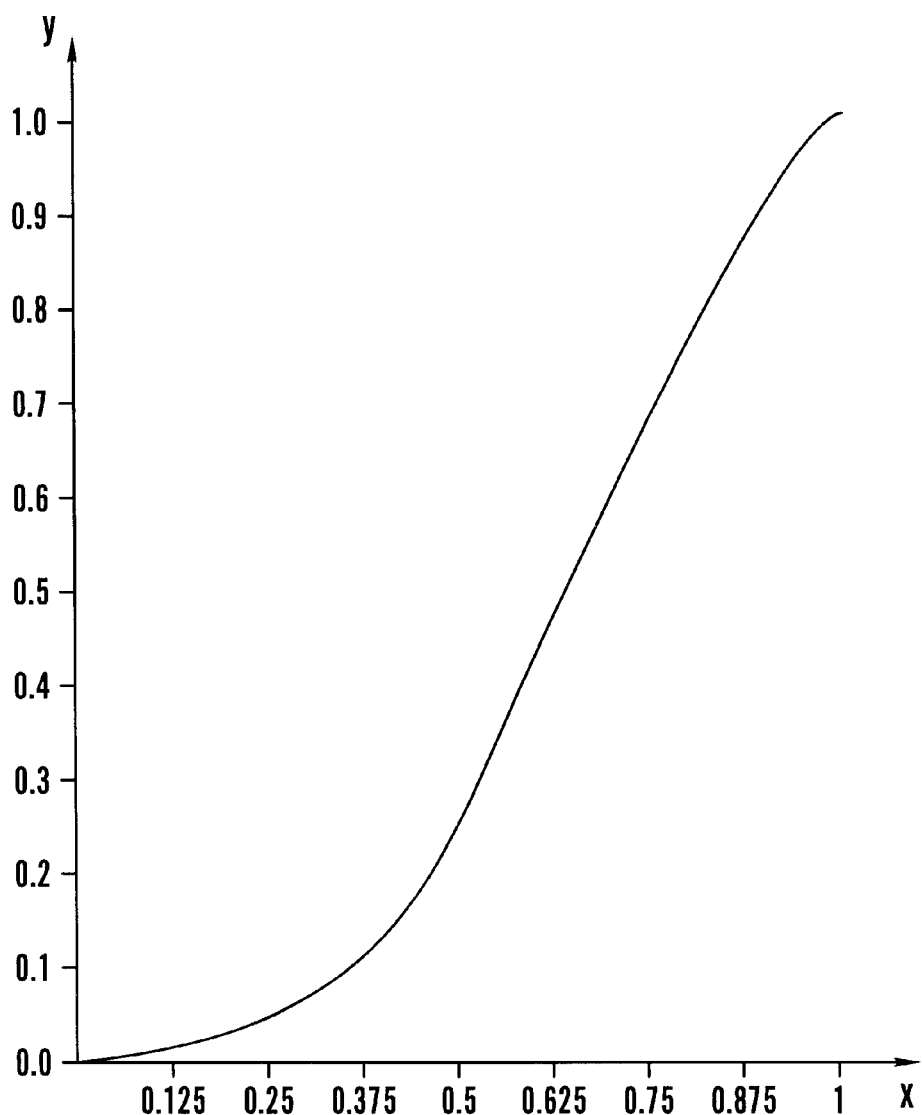
Figure 10:
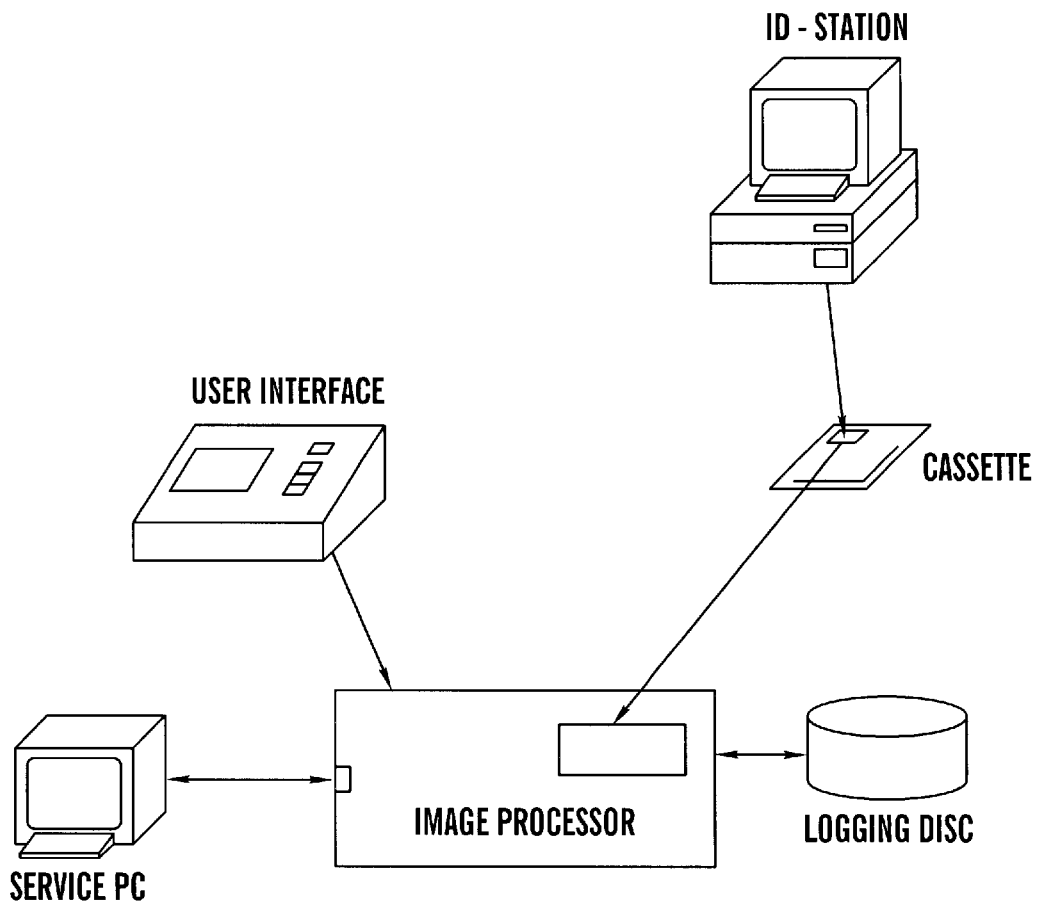
Figure 11:
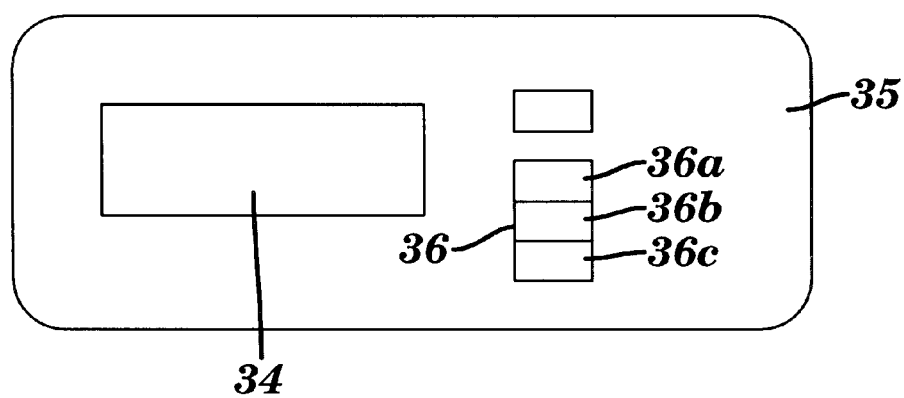

Particular embodiments of the present invention will be explained with reference to the drawings in which FIG. 1 generally shows a system in which the present invention can be applied, FIG. 2 is specific embodiment of an image acquisition apparatus, FIGS. 3a and 3b schematically illustrate the data processing performed on the read-out image signal, FIG. 4 is a representation of an image enhancement and noise reduction system, FIG. 5 is a specific embodiment of a decomposition system, FIG. 6 is a specific embodiment of a noise reduction process, FIG. 7 is a specific example of a modifying function, FIG. 8 is a specific embodiment of an image reconstruction system, FIG. 9 is a plot of a canonical curve used in determining a mapping curve, FIG. 10 is an illustration of the different modalities of output of stored information, FIG. 11 shows the lay-out of a user interface.

FIG. 1 shows a system in which the present invention can be applied. A radiation image of an object was recorded on a photostimulable phosphor screen (3) by exposing (2) said screen to x-rays transmitted through an object (not shown). The stimulable phosphor screen was conveyed in a cassette (3) provided with an electrically erasable programmable read-only memory (EEPROM). In an identification station (4) various kinds of data (name, date of birth etc) and data relating to the exposure and/or to the signal processing were recorded onto the EEPROM.

In a radiation read-out apparatus (1) the latent image stored on the photostimulable phosphor screen was read-out.

Then the image signal was sent to the image processor (7) where it can be stored on the system disc. The signal was also sent to the review console (5) where it was temporarily stored on a hard disc. This back up ensures that the signal is not lost and can be retrieved for any kind of later processing, for example processing with different parameter setting. After processing the image signal was sent to an output device (6) more specifically a laser recorder.

FIG. 2 shows one embodiment of an image read-out unit. This figure shows a photostimulable phosphor screen 8 that has been exposed to an X-ray image of an object.

In the radiation image readout apparatus the latent image stored in the photostimulable phosphor screen is read out by scanning the phosphor sheet with stimulating rays emitted by a laser 9. The stimulating rays are deflected according to the main scanning direction by means of a galvanometric deflection device 10. The secondary scanning motion is performed by transporting the phosphor sheet in the direction perpendicular to the scanning direction. A light collector 11 directs the light obtained by stimulated emission onto a photomultiplier 12 where it is converted into an electrical signal, which is next sampled by a sample and hold circuit 13, and converted into a 12 bit digital signal by means of an analog to digital converter 14. The signal is also applied to a square root amplifier so that the output image representing signal also called 'original or raw' image is a 12 bit signal which is proportional to the square root of applied exposure values and represents the pixel value in 2048×2496 pixels.

From the output of the read-out apparatus the original image is sent to an image processor (numeral 7 in FIG. 1).

The sequence of the different processing steps performed on the image signal is illustrated in FIG. 3.

First the histogram of the unmodified original image is calculated and stored on the system disc (indicated by numeral 7' in FIG. 1).

Next, the original image is subjected to noise suppression and contrast enhancing processing as schematically shown in FIG. 4. The image enhancement section comprises four main parts. In a decomposition section 15 the original image is decomposed into a sequence of detail images 16, which represent the amount of detail present in the original image at multiple resolution levels, from fine to coarse. After the last decomposition step a residual image 17 may be left.

The noise suppression section 18 modifies the resulting detail images 16, which represent the amount of local detail at successive resolution levels according to the locally estimated amount of signal content.

The thus modified detail images 19 are next subjected to contrast enhancement in section 20 by pixel-wise modification according to a non-linear mapping function.

Next, the modified images 21 are applied to an image reconstruction section 22 wherein the modified detail images 21 are accumulated at all resolution levels, along with the residual image 17 to compute the enhanced image 23.

A specific embodiment of the decomposition process is depicted in FIG. 5. The modifying section and the reconstruction section will be described furtheron.

In the decomposition section the original image is filtered by means of a low pass filter 26, and subsampled by a factor of two, which is implemented by computing the resulting low resolution approximation image $g_1$ only at every other pixel position of every alternate row. A detail image $b_0$ at the finest level is obtained by interpolating the low resolution approximation $g_1$ with doubling of the number of rows and columns, and pixelwise subtracting the interpolated image from the original image.

The interpolation is effectuated by the interpolator 27, which inserts a column of zero values every other column, and a row of zero values every other row respectively, and next convolves the extended image with a low pass filter. The subtraction is done by the adder 28.

The same process is repeated on the low resolution approximation $g_1$ instead of the original image, yielding an approximation of still lower resolution $g_2$ and a detail image $b_1$.

A sequence of detail images $b_i$, i=0 ... L−1 and a residual low resolution approximation $g_L$ are obtained by iterating the above process L times.

The finest detail image $b_0$ has the same size as the original image. The next coarser detail image $b_1$ has only half as many rows and columns as the first detail image $b_0$. At each step of the iteration the maximal spatial frequency of the resulting detail image is only half that of the previous finer detail image, and also the number of columns and rows is halved, in accordance with the Nyquist criterion. After the last iteration a residual image $g_L$ is left which can be considered to be a very low resolution approximation of the original image. In the extreme case it consists of only 1 pixel which represents the average value of the original image In a great deal of the radiologic examination types the patient is protected against unnecessary exposure to x-rays by means of an x-ray opaque (collimation) material that is placed in the x-ray beam path for shielding the diagnostically irrelevant parts of the patient.

However, the image data originating from the image part corresponding with the collimation material have an influence on the processing. Furthermore, when reproduced unmodified, the part of the image corresponding with the collimation material may cause problems in the display, for example it may impair diagnosis of subtle lesions due to dazzle since the unexposed image parts appear very bright. So, it is advantageous to exclude the data regarding the collimation material from further consideration during processing.

Hence a method has been developed for determining the signal/shadow boundary in an image so as to recognize the exact limits of the irradiation field, this method has been described in extenso in our copending application entitled "Method of recognising an irradiation field" and filed on the even day.

According to this method many hypotheses (being a segmentation of an image into signal and shadow regions) as to the location of the signal/shadow boundary are built from combinations of intermediate level primitives. These intermediate level primitives are for example extended line segments. Each proposed hypothesis is subjected to a number of tests so as to detect and reject an incorrect hypothesis; non-rejected hypotheses are then ranked in order that a single candidate may be chosen.

For the purpose of reducing the computational effort, the location of the irradiation field is calculated by applying the above method to one the low resolution images resulting from the decomposition processing described hereinbefore, namely on a low resolution image comprising 256×312 pixels (8 bit representation), this image is used as an operational tool for determining the irradiation field, furtheron called "the region of interest", this low resolution image serves as a 'reduced image version' and is stored on the system disc.

The method described higher for delineating the image region of diagnostic interest results in an overlay image with the same number of elements as the low resolution image. The resulting overlay image is interpolated so as to represent 2048×2496 pixels, a number equal to the number of pixels in the original image. The non-interpolated overlay image is stored for later use when determining the histogram of the region of interest in the processed image, as will be described furtheron.

The detail images resulting from the decomposition step are also subjected to noise suppression processing. An embodiment of a noise suppressing section comprising a section wherein the noise variance is estimated, is illustrated in FIG. 6.

Numeral 31 is a memory wherein the detail images $b_i$ and the residual image $g_L$ resulting from the image decomposition are stored. Each detail image is pixelwise transferred to a squaring unit 32, starting with the coarsest detail image. A moving average operator 33 then computes the local variance v at every pixel position by summing all squared pixels in an N×N neighborhood centered around the current target pixel (a neighborhood of 15×15 elements proved to be adequate), and dividing the sum by the number of pixels in the neighborhood. These local variance pixels are temporarily stored in a memory device 34 and transferred at the same time to a histogram computation circuit 35. A histogram is an array, the elements of which are called bins, each bin corresponding to a fixed sampling interval of the signal range associated with the horizontal histogram axis. Each bin resides in a memory cell, all of them being initialised to zero before accepting the first pixel. For each entered variance value the histogram computation circuit selects the corresponding bin index and increments the associated bin value by one.

After all pixels of a variance image at a particular resolution level have been used in this way, the histogram represents the occurence of every quantised variance value throughout the image. This local variance histogram is next supplied to a maximum locator 36 which determines the variance value with the highest occurence $v_n$ in the histogram. This value is used as an estimate for the noise variance within the considered detail image.

This estimated value is one of the parameters that is stored in the sequentially organised storage device according to the present invention on the system disc.

The noise variance $v_n$ determined by the maximum locator is used as a parameter in the noise suppression function $S_{v_n}(v)$, which is defined as:

$S_{v_n}(v) = 0$ if $v <= K^*v_n$ $S_{v_n}(v) = 1 - K^*v_n/v$ otherwise where K is a fixed noise suppression factor which determines the amount of noise suppression to be applied; K=0 implies no noise suppression (numeral 37).

This function is computed and installed as a noise suppression look-up table for every detail image within the decomposition. When a noise suppression look up table corresponding to a particular resolution level has been installed, all variance pixels corresponding with the same level are fetched from the memory and tranformed into a sequence of attenuation coefficients. The resulting pixels are computed by pixelwise multiplying (38) these coefficients with the pixels of the detail image at the same level, fetched from the memory 31.

This whole process is repeated for all detail images up to the finest level, to yield attenuated detail images.

The next processing step is the contrast enhancement step which is performed by modifying the pixels of the detail images (after noise suppression) to yield pixel values of a set of modified detail images according to at least one non-linear monotonically increasing odd mapping function with a slope that gradually decreases with increasing argument values.

A preferred embodiment of the modification section 20 in FIG. 4 comprises a memory for temporarily storing the detail images 19 and the residual image 17, and a lookup table which converts every pixel value x of each detail image into an output value y according to the function:

$$y = -m*(-x/m)^P \text{ if } x<0$$

$$y = m*(x/m)^P \text{ if } x>=0$$

where the power p is chosen within the interval 0<p<1, preferably within the interval 0.5<p<0.9. A comparative evaluation of a large number of computed radiography images of thorax and bones by a team of radiologists indicated that p=0.7 is the optimal value in most cases. m specifies the abscissa range: −m<=x<=m, e.g. m=4095 if detail pixels are represented by 13 bits signed.

A plot of the above function is presented in FIG. 7.

Next, the inverse transformation providing the image reconstruction is applied, one embodiment of an implementation of the reconstruction process is depicted in FIG. 8.

The residual image is first interpolated by interpolator 41 to twice its original size and the interpolated image is next pixelwise added to the detail image of the coarsest level $b'_{L-1}$ using adder 42. The resulting image is interpolated and added to the next finer detail image. When this process is iterated L times using the unmodified detail images $b_{L-1} \ldots b_0$ then the original image will result. When at the other hand the detail images are modified before reconstruction according to the findings of the present invention, then a contrast enhanced image will result. The interpolators 41, 41' ... are identical to those used in the decomposition section.

After reconstruction the image is subjected to a logarithmic conversion and the processed image is finally stored.

For hard copy recording or display the processed image is subjected to a signal-to-density conversion on the basis of a mapping curve defining the relation between the individual signal values and the correspondingly envionsoned density value. Parameters for defining the mapping curve are deduced from analysis of the histogram of the region of interest in the processed image. This region of interest is determined by selecting out of the pixels of the processed image only these pixels that belong to the image area defined by the overlay image produced hereinbefore, the pixels of the region of interest in the processed image are then applied to a histogram calculation circuit, the calculated histogram is part of the intermediate processing results that are stored in the sequential storage device on the system disc.

In a following processing step this histogram is analysed so as to determine the limits of the signal range relevant for display or reproduction.

The analysis of the histogram is performed as described in our application EP 91203212.5 filed on Dec. 9, 1991 and U.S. Ser. No. 07/978,786. The analysis of the histogram results in the definition of a signal range to be extracted for further processing, this range is obtained by performing the steps of determining the maximum histogram frequency, selecting a value t smaller than the maximum histogram frequency, determining (a) histogram peak(s) as a range of successive signal values having a corresponding histogram frequency that is larger than t, determining the most relevant histogram peak as the histogram peak for which the summation of all histogram frequencies corresponding with signal values within said peak is maximum, determining minimum and maximum signal values within said most relevant histogram peak, and determining extreme values of the signal range to be extracted as said minimum value decreased with a small offset do and said maximum value increased by a small offset value $d_1$.

For example $d_0$ was equal to 0.2 log exposure units, $d_1$ was equal to 0.1 log exposure units.

Next, the extracted signal range is used in the process of defining the mapping curve as described in our European application EP 91203209.1 filed Dec. 9, 1991 ans U.S. Ser. No. 07/978,091. The mapping curve was determined as follows:

First the minimum density value $D_{smin}$ and the maximum density value $D_{smax}$ envisioned in the hard copy were defined, $D_{smin}$ was equal to fog density and $D_{smax}$ was equal to 3.0. These parameters were obtained from a parameter table and are a function of the examination type.

Then a canonical function defined in an orthogonal coordinate system between $x_0$, $x_1$ and $Y_{min}, y_{max}$ was retrieved from the internal memory of the signal processor. This function is also function of the examination type. A plot of such a function is shown in FIG. 9.

Next two values $S_{min}$ and $S_{max}$ were determined that constitute a range wherein the conversion of signal values onto density values is determined by the specific shape of the canonical function. Signal values smaller than $S_{min}$ are mapped onto $D_{smin}$, signal values greater than $S_{max}$ are mapped onto $D_{smax}$.

In this embodiment the latitude of said range was a fixed value L=1.5 log exposure (corresponding with the latitude of a conventional x-ray film the radiologist is used to work with) and the position of $S_{min}$ was determined relative to the diagnostically relevant signal range. $S_{max}$ was then calculated as $S_{min}+L$. For determining the position of $S_{min}$ relative to the relevant signal range, the extreme values $S_0$ and $S_1$ of the diagnostically relevant signal range were first determined by evaluation of the image histogram.

Then a small offset $dS_1=0.3$ log E was added to $S_1$. This ensures that the density in the hard copy corresponding with the maximum value of the diagnostically relevant signal range does not become too dark.

The positioning of the range $S_{max}-S_{min}$ relative to the range $S_1-S_0$ was performed by aligning a fraction of the latter range with the same fraction of the former range.

Mathematically this fraction can be expressed as $A(S_1+dS_1-S_0-dS_0)$. Then the alignment can be formulated mathematically as $S_{min}=S_0+dS_0+A(S_1+dS_1-S_0-dS_0)-A.L$ and $S_{max}=S_{min}+L$, A being an integer value greater than or equal to 0 and smaller than or equal to 1.

Next a look up table representing the mapping curve is composed and stored.

The parameters $S_0$, $S_1$, $S_{min}$, $S_{max}$ and the mapping curve are stored on the system disc.

Finally the mapping curve is applied to the part of the processed image within the region of interest defined by application of the extrapolated overlay image so as to obtain the output image.

FIG. 10 illustrates that the patient's identification data as well as an identifier referring to a specific preset type of processing relating to a specific examination type were written into an EEPROM on a cassette conveying a photostimulable phosphor screen. In the read-out device shown in FIG. 1 (numeral 1) these data were read-out from the EEPROM. Then in the image processing unit the image was decomposed into a sequence of detail images at multiple resolution levels and a residual image and the detail images were processed taking into account processing parameters corresponding with the identifier read out of the EEPROM, the processing parameters being retrieved from a parameter table.

Next, the identification data, at least one of the low resolution images obtained during image decomposition and the following intermediate processing results were stored on the system disc: original image histogram, $n_{var}$, histogram of processed image, $S_{min}$, $S_{max}$, $S_0$, $S_1$, and the mapping curve.

The figure illustrates that a service PC can be connected to the processing unit for uploading the stored data and that the earlier mentioned scroll and freeze commands can be activated on a user interface as shown in FIG. 11.

This user interface permits the operator to display identification data of consecutively stored images, to control read-out of the stored data and to output selected data.

To this end this user interface comprises a display section 34, a scroll option 35 which permits the operator to scroll through and display the identification data associated with stored sets of data (namely sets of the identification data, a reduced image version, processing parameters and intermediate processing results) and to select identification data, for example data corresponding with an image that needs to be evaluated.

This user interface additionally comprises an output command function 36 which upon activation controls retrieval of stored data corresponding with an identified image from the storage device and output to the selected output modality. In this embodiment the output modalities are either display (via function 36a) on a monitor, output through printing (function 36b), or transfer to an external storage medium such as a disc in a service personal computer (function 36c).

What is claimed is:

1. An apparatus for evaluating image processing performed on a plurality of original radiographic images each stored on a different photostimulable phosphor screen, comprising:

means for scanning each screen with stimulating radiation;

means for detecting the light emitted from each screen upon stimulation;

means for converting the detected light emitted from each screen into a digital signal representation of the original radiographic image stored on the screen;

means for determining a set of processing parameters for each original radiographic image;

means for processing the digital signal representation of each original radiographic image on the basis of the set of processing parameters determined for the image;

means for deducing from the digital signal representation of each original radiographic image a reduced version representing a reduced number of pixels;

means for storing an evaluation data record for each of the plurality of original radiographic images, the evaluation data record for each image comprising data identifying the image, the set of processing parameters for the image, intermediate processing results for the image, and the reduced version of the image;

means for identifying one of the plurality of original radiographic images to be evaluated;

means for retrieving the evaluation data record pertaining to the identified image; and means for generating an output of the contents of the retrieved evaluation data record.

2. An apparatus according to claim 1 wherein said means for storing the evaluation data record for each of the plurality of original radiographic images is a sequentially organized storage device capable of storing data pertaining to N read-out images, said storage device being organized so that data originating from a N+1-th read-out image is stored at the expense of data originating from a first of N read-out images.

3. An apparatus according to claim 2 comprising control means which upon activation prohibit shift out of the evaluation data record pertaining to at least one identified image from said storage device.

4. An apparatus according to claim 1 wherein said means for identifying one of the plurality of original radiographic images to be evaluated comprises:

means for displaying stored identification data, and means for scrolling through said displayed identification data and for controlling retrieval of the evaluation data record corresponding to the displayed identification data.

5. An apparatus according to claim 1 wherein said means for generating an output is a hard copy recorder.

6. An apparatus according to claim 1 wherein said means for generating an output is a personal computer.

7. An apparatus for evaluating image processing performed on a plurality of original radiographic images each stored in a different radiographic film, comprising:

means for scanning each film with a light beam;

means for detecting the light modulated by the image in each film;

means for converting the image-wise modulated light into a digital signal representation of the original radiographic image stored in each film;

means for determining a set of processing parameters for each original radiographic image;

means for processing the digital signal representation of each original radiographic image on the basis of the set of processing parameters determined for the image;

means for deducing from the digital signal representation of each original radiographic image a reduced version representing a reduced number of pixels;

means for storing an evaluation data record for each of the plurality of original radiographic images, the evaluation data record for each image comprising data identifying the image, the set of processing parameters for the image, intermediate processing results for the image, and the reduced version of the image;

means for identifying one of the plurality of original radiographic images to be evaluated;

means for retrieving the evaluation data record pertaining to the identified image; and means for generating an output of the contents of the retrieved evaluation data record.

8. An apparatus according to claim 7 wherein said means for storing the evaluation data record for each of the plurality of original radiographic images is a sequentially organized storage device capable of storing data pertaining to N read-out images, said storage device being organized so that data originating from a N+1-th read-out image is stored at the expense of data originating from a first of N read-out images.

9. An apparatus according to claim 8 comprising control means which upon activation prohibits shift out of the evaluation data record pertaining to at least one identified image from said storage device.

10. An apparatus according to claim 7 wherein said means for generating an output is a hard copy recorder.

11. An apparatus according to claim 7 wherein said means for generating an output is a personal computer.

12. An apparatus according to claim 7 wherein said means for identifying one of the plurality of original radiographic images to be evaluated comprises:

means for displaying stored identification data, and means for scrolling through said displayed identification data and for controlling retrieval of the evaluation data record corresponding to the displayed identification data.

13. An apparatus for evaluating image processing performed on a plurality of original radiographic images each stored on a different photostimulable phosphor screen, comprising:

a radiation read-out unit for scanning each screen with stimulating radiation, for detecting the light emitted from each screen upon stimulation, and for converting the detected light emitted from each screen into a digital signal representation of the original radiographic image stored on the screen;

an image processor for determining a set of processing parameters for each original radiographic image, for processing the digital signal representation of each original radiographic image on the basis of the set of processing parameters determined for the image, and for deducing from the digital signal representation of each original radiographic image a reduced version representing a reduced number of pixels;

data storage for storing an evaluation data record for each of the plurality of original radiographic images, the evaluation data record for each image comprising data identifying the image, the set of processing parameters for the image, intermediate processing results for the image, and the reduced version of the image;

a system for identifying one of the plurality of original radiographic images to be evaluated;

a system for retrieving the evaluation data record pertaining to the identified image; and an output device for generating an output of the contents of the retrieved evaluation data record.

14. The apparatus according to claim 13 wherein said data storage for storing the evaluation data record for each of the plurality of original radiographic images is a sequentially organized storage device capable of storing data pertaining to N read-out images, said storage device being organized so that data originating from a N+1-th read-out image is stored at the expense of data originating from a first of N read-out images.

15. The apparatus according to claim 14 further comprising a control system which upon activation prohibits shift out of the evaluation data record pertaining to at least one identified image from said storage device.

16. The apparatus according to claim 13 wherein said system for identifying one of the plurality of original radiographic images to be evaluated comprises:

a display for displaying stored identification data, and a system for scrolling through said displayed identification data and for controlling retrieval of the evaluation data record corresponding to the displayed identification data.

17. The apparatus according to claim 13 wherein said output device for generating an output is a hard copy recorder.

18. The apparatus according to claim 13 wherein said output device for generating an output is a personal computer.

* * * * *